United States Patent [19]

Jenkins et al.

[11] Patent Number: 5,007,072
[45] Date of Patent: Apr. 9, 1991

[54] X-RAY DIFFRACTION INSPECTION SYSTEM

[75] Inventors: Anthony Jenkins, Medford, Mass.; Peter W. Stephens, Stony Brook, N.Y.

[73] Assignee: Ion Track Instruments, Wilmington, Mass.

[21] Appl. No.: 227,722

[22] Filed: Aug. 3, 1988

[51] Int. Cl.⁵ .................................. G01N 23/201
[52] U.S. Cl. ................................ 378/88; 378/57
[58] Field of Search .................... 378/70, 71–73, 378/79, 80, 86, 88, 208, 82, 83, 57; 250/370.10

[56] References Cited

U.S. PATENT DOCUMENTS

| Re. 28,544 | 9/1975 | Stein et al. | 250/369 |
|---|---|---|---|
| 3,428,802 | 2/1969 | Mehta et al. | 378/71 |
| 3,440,419 | 4/1969 | Das Gupta et al. | 378/71 |
| 3,596,092 | 7/1971 | Marjoram | 378/71 |
| 3,759,383 | 9/1973 | Inoue | 378/71 |
| 3,895,232 | 7/1975 | Schneeberger | 250/366 |
| 3,980,889 | 9/1976 | Haas et al. | 250/492 |
| 4,020,346 | 4/1977 | Dennis | 250/358 |
| 4,031,545 | 6/1977 | Stein et al. | 358/108 |
| 4,131,794 | 12/1978 | Bruninx | 378/83 |
| 4,228,357 | 10/1980 | Annis | 250/445 |
| 4,260,898 | 4/1981 | Annis | 250/505 |
| 4,303,860 | 12/1981 | Bjorkholm et al. | 250/363 |
| 4,342,914 | 8/1982 | Bjorkholm | 378/99 |
| 4,357,535 | 11/1982 | Haas | 378/57 |
| 4,389,729 | 6/1983 | Stein | 378/99 |
| 4,430,568 | 2/1984 | Yoshida et al. | 378/57 |
| 4,454,605 | 6/1984 | DeLucia | 378/57 |
| 4,511,799 | 4/1985 | Bjorkholm | 250/367 |
| 4,691,332 | 9/1987 | Burstein et al. | 378/7 |
| 4,715,053 | 12/1987 | Comstock et al. | 378/71 |
| 4,751,722 | 6/1988 | Harding et al. | 378/88 |
| 4,799,247 | 1/1989 | Annis et al. | 378/86 |

OTHER PUBLICATIONS

*J. Opt. Soc. Am. A;* "Status and Outlook of Coherent X-Ray Scatter Imaging"; G. Harding and J. Kosanetzky; vol. 4, No. 5; May 1987; pp. 933–944.

*Newsweek;* "Detecting Concealed Weapons"; Jun. 23, 1986; p. 3.

*American Science and Engineering, Inc.;* "Z Technology".

"Heimann HI-SCAN X-Ray Scanning Systems the Best Solution to Increase the Efficiency of Your Security Force"; 4 pages.

*Primary Examiner*—Craig E. Church
*Attorney, Agent, or Firm*—Hamilton, Brook, Smith & Reynolds

[57] ABSTRACT

An inspection system for detecting the presence of selected crystalline materials, such as explosives or drugs, utilizing an x-ray source and a collimated array of detectors to sense radiation scattered by the objects being inspected. A signal processing system compares the measured signal with selected spectra to determine whether specific materials are present within the inspected object.

15 Claims, 5 Drawing Sheets

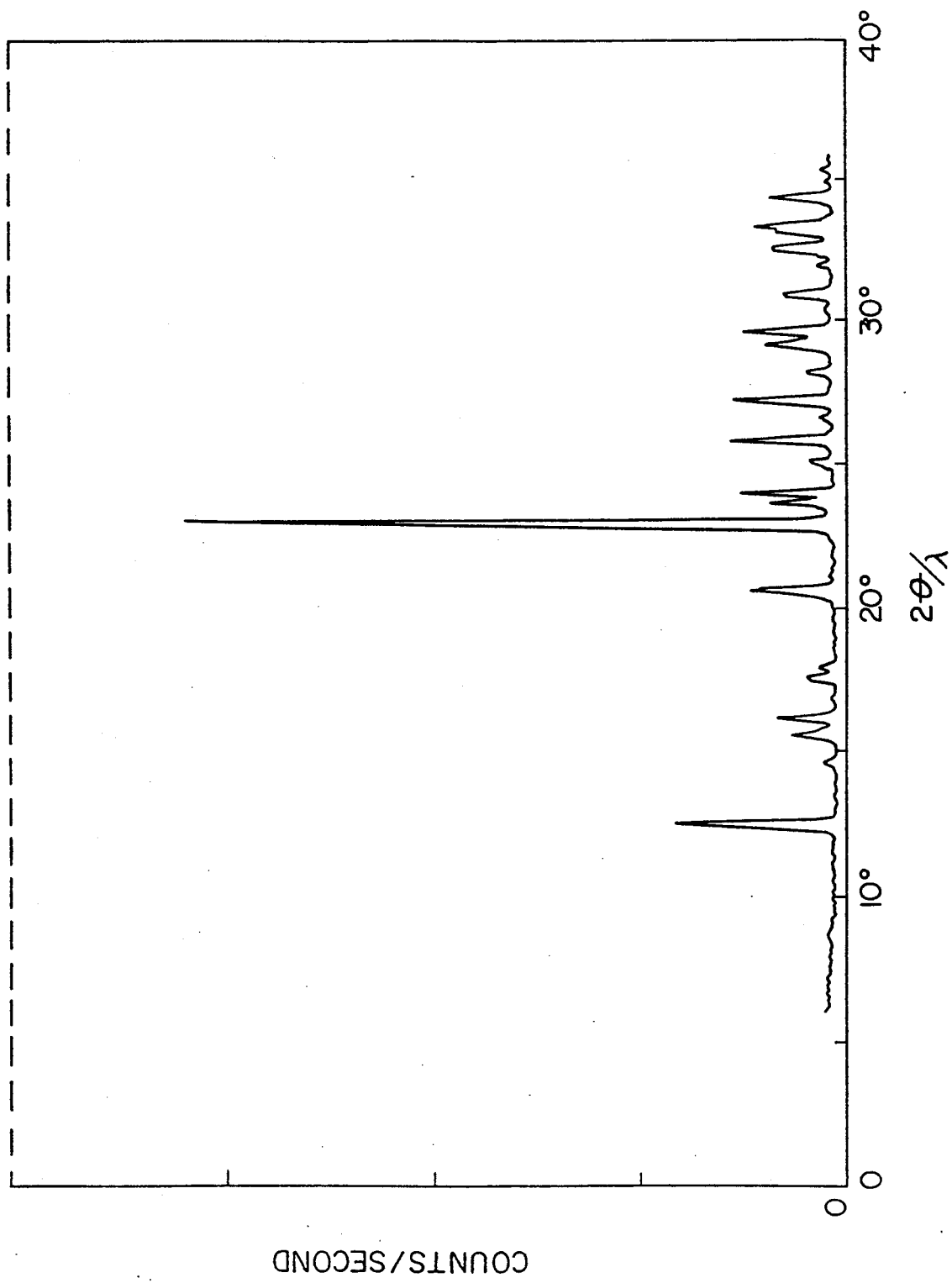

X-RAY DIFFRACTION INSPECTION SYSTEM

BACKGROUND OF THE INVENTION

The invention relates generally to the field of radiographic detection systems, and more particularly, to coherent x-ray scattering systems used to inspect objects to detect the presence of explosive materials.

Numerous systems have been developed for the inspection of bags, suitcases and briefcases etc. that are used to screen travelers at airports or to secure other types of installations. Of particular concern in the development of such systems has been the detection of concealed weapons, explosives or drugs whose transport is restricted. Typically, standard x-ray equipment has been used to scan for metal objects where the outline of the displayed items is visually inspected to determine the presence of the objects of concern. These systems use a conveyor to transport the item to be inspected into and out of a chamber positioned between an x-ray source and a fluoroscopic or scintillation screen that detects the transmitted radiation. These inspection systems must be safe for the operators, and must not damage items such as photographic film that are often contained in inspected baggage.

Unfortunately, many kinds of materials that may pose a danger may not conform to any easily identifiable shape and are not visually detectable in the systems currently in use. In particular, many types of explosive materials in use can be molded into any shape and are not detectable by standard x-ray equipment. Thus, there is a need for a more accurate and dependable system for detecting these materials.

SUMMARY OF THE INVENTION

The inspection device of the present invention utilizes an x-ray radiation source to scan objects to determine whether certain crystalline substances are contained therein. Most explosives and many other dangerous or illegally transported substances have a crystalline structure.

Crystalline materials are known to scatter radiation when illuminated by an x-ray source of suitable energy and spectral content. Coherent elastic scattering of radiation occurs from lattices of spacing "d" within the crystalline material which satisfy the equation $\lambda = 2d \sin\theta$ where the wavelength and $2\theta$ is the angle of diffraction of the scattered radiation away from an axis through the source and the area being scanned. Thus, elastic scattering will occur at a few select wavelengths whereas inelastic scattering by the atoms of the material will occur continuously across a spectrum of wavelengths.

A detector positioned at the appropriate angle relative to the source and scanned object is fitted with a collimator that permits only those x-rays diffracted at that angle to reach the detector. The detector is preferably comprised of a photon spectrometer. Such spectrometers provide both intensity and spectral composition of the detected radiation and are typically either solid state germanium or silicon planar arrays operated at cryogenic temperatures.

Each scattered photon is detected individually and a wavelength spectrum of intensities, displayed as an energy dispersive spectrum, is generated by a signal processing circuit.

A peak comparator algorithm incorporated into a data processing system is applied to the spectral output to determine the presence of sharp peaks within the spectrum. By comparing the peaks from the processed spectrum with the spectrum of crystalline substances sought to be detected the presence of those materials within the object is determined with great accuracy.

The above, and other features of the invention including various novel details of construction and combination of parts, will now be more particularly described with reference to the accompanying drawings and pointed out in the claims. It will be understood that the particular x-ray detection system embodying the invention is shown by way of illustration only and not as a limitation of the invention. The principle features of this invention may be employed in various embodiments without departing from the scope of the invention.

BRIEF DESCRIPTION OF THE DRAWINGS

FIGS. 3a, 3b and 3c are illustrative graphical representations of diffraction spectra of particular explosive materials.

DETAILED DESCRIPTION

The detection system of the present invention is comprised of energy dispersive X-ray detectors arranged to measure the coherent elastic scattering of x-ray photons from the lattices of crystalline materials and in particular of crystalline explosives and of narcotic or hallucinogenic drugs. Nearly all of the explosives of interest comprise crystalline powders. For example, the plastic explosives are manufactured from crystalline powders of cyclotrimethyline-trinitramine (RDX), cyclotetramethyline tetranitramine (HMX) and pentaerithritol tentranitrate (PETN), and are compounded into a putty with minor amounts of organic binders. Each of the explosives which are to be detected provides a unique diffraction pattern when irradiated with x-rays such that each may be rapidly identified. The only notable exceptions are the nitro-glycerine-based dynamites. Fortunately these explosives are easy to detect by their vapor emissions and the two detection systems can be combined into a single instrument.

Figure 2:
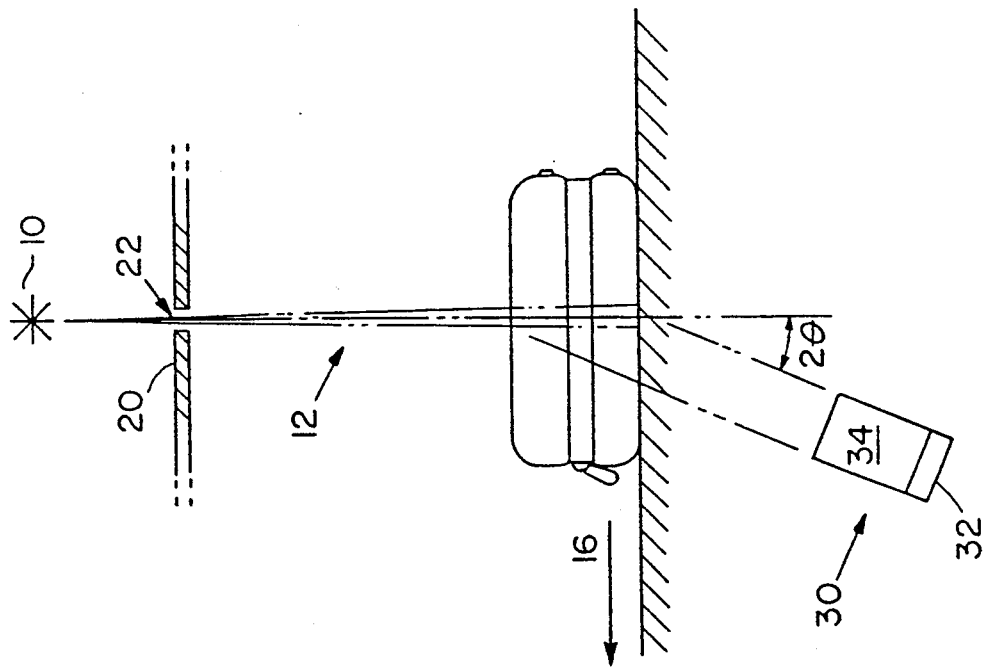
FIG. 2 shows a side view of the system shown in FIG. 1.
Figure 1:
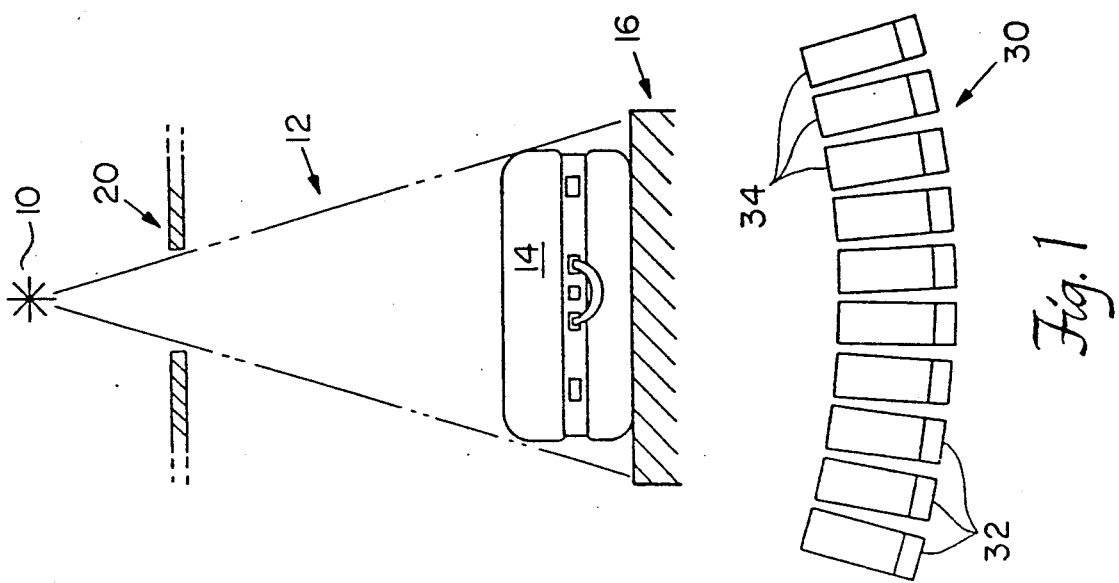
FIG. 1 illustrates a front schematic view, of a preferred embodiment of the invention.

A schematic illustration of a preferred embodiment of the system is shown in FIGS. 1 and 2. This system has sufficient speed of response to detect explosives in bags which are conveyed through the detection zone in a few seconds. X-rays from source 10 are arranged in a beam 12 having a fan pattern to irradiate a bag 14 which are conveyed along conveyor 16 through the beam 12. The beam 12 comprises an x-ray continuum whose range of photon energies is sufficient to penetrate large checked bags. The beam 12 is produced by collimation of the single x-ray source 10 of constant potential with slit collimator 20.

Photons scattered elastically from the crystalline lattice of explosives interferes coherently depending on the lattice structure, the frequency and angle of scatter. At a fixed angle of scatter, scattered rays comprise a continuum from non-crystalline materials and photons which are coherently scattered from the various 'd' spacings of the crystals. In a typical two dimensional lattice there are three major 'd' spacings which allow coherent diffraction. There are other lattice spacings in the third dimension so that for randomly oriented crystals there are sufficient 'd' spacings to provide a unique set, but not so many that they cause an overly cluttered diffraction spectrum.

The x-rays scattered in a beam of fixed angle defined by the detector collimator 34 comprises a continuum with superimposed intensity peaks at wavelengths $\lambda_1 \ldots n$.

The detection system 30 measures the intensity of scattered light in intervals of wavelengths over a wide range of photon energies but at a fixed angle $2\theta$ of scatter. This provides a unique fingerprint for each type of explosive.

An array of individual detectors 32 is arranged across the full width of a conveyor system irradiated by an x-ray fan beam 12. This permits scanning of the whole volume of the bag 14.

In a preferred embodiment the detector 32 employed in the system is a planar germanium photon spectrometer. These detectors operate as photon counters by detecting the liberation of free electrons by an x-ray photon in a germanium semiconductor. The total charge liberated by each x-ray photon is indicative of the photon energy thus allowing an intensity spectrum to be generated over a range of x-ray wavelengths. Typical resolution (full-width-half-maximum) provided by commercial detectors is 500 eV at 120 KeV photon energy. The detector for this embodiment has a 100% detection efficiency over a range of photon energy from 5 KeV to 120 KeV.

The system is based on the detection of presence of two or three peaks in the spectrum. It is unlikely that the detection of these peaks will be interfered with by other crystalline materials. For example, the only crystalline material normally encountered in detectable quantities in 99% of airline bags are the metals aluminum, steel, and copper. The sensitivity of the inspection system is proportional to the total amount of crystalline material in a bag, so for small amounts of these metals only a low intensity of scatter is expected and this information is in parts of the spectrum which are distinct from the explosives or drugs of interest. Large amounts of metal can possibly stop 120 KeV photons and this condition can be detected by the attenuation of the transmitted beam in a similar way to standard airport baggage x-rays, but no image would be generated. This condition is not expected to exist in more than a fraction of a percent of airline bags, and of course attempts to conceal the explosive by this method results in a rejection because of too high a metallic content.

The principle of detection is to send a "white" x-ray beam 12, containing a range of wavelengths, through the specimen and look for diffracted radiation at a fixed angle $2\theta$, with a detector system 30 that simultaneously measures intensity and wavelength. The advantages of energy dispersive x-ray diffraction over the more common monochromatic powder technique are two fold: the large sensitive volume (and therefore freedom from the necessity of aligning the sample precisely), and the fact that an entire spectrum may be collected in parallel.

In a crystal, there are regular planes of atoms separated by well defined distances $d_1 \ldots n$. X-rays of wavelength $\lambda$ may be scattered by these planes through a total angle $2\theta$ if they meet the diffraction condition.

$$\lambda = 2 d \sin\theta$$

Figure 3B:
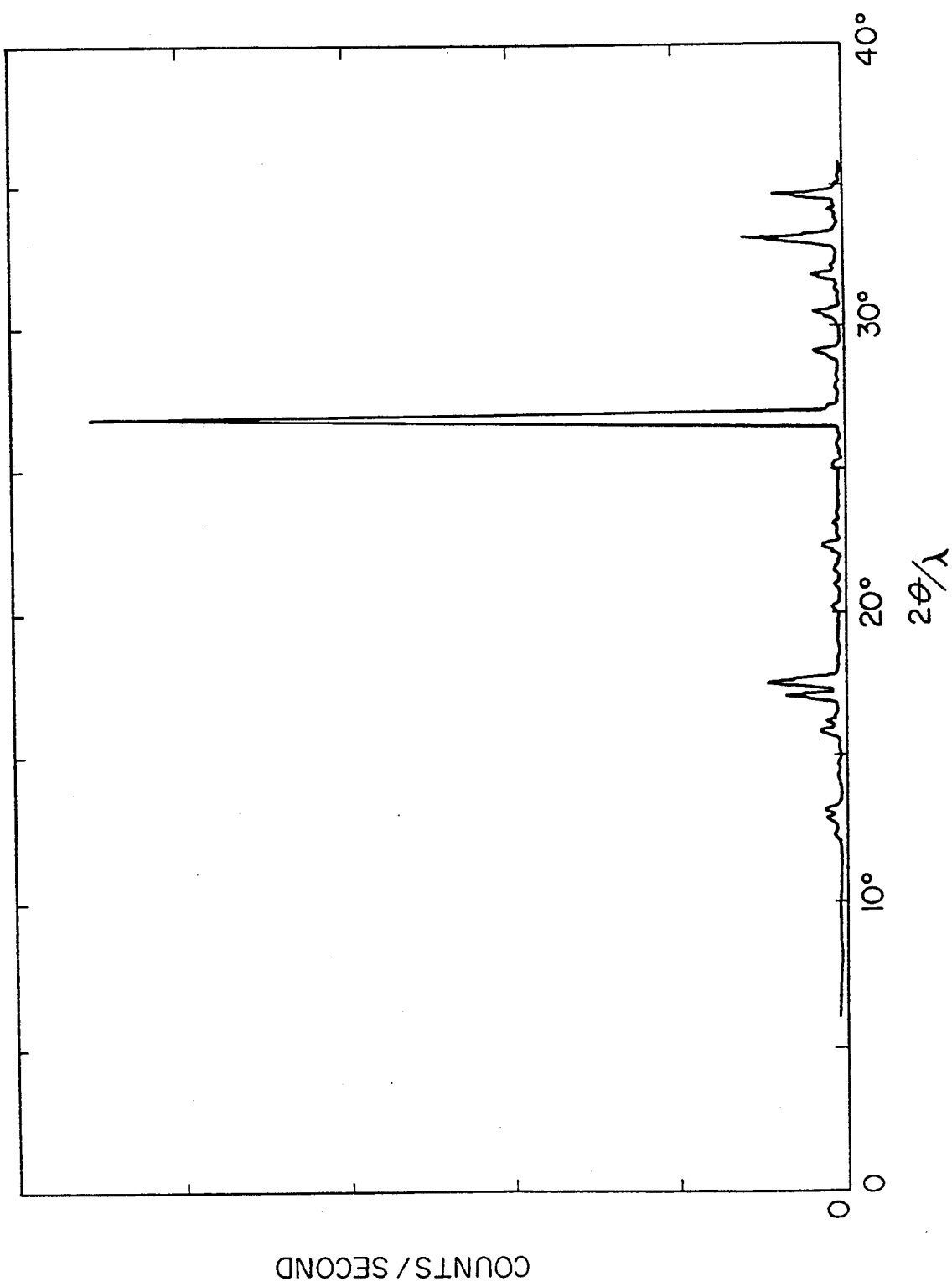
Figure 3C:
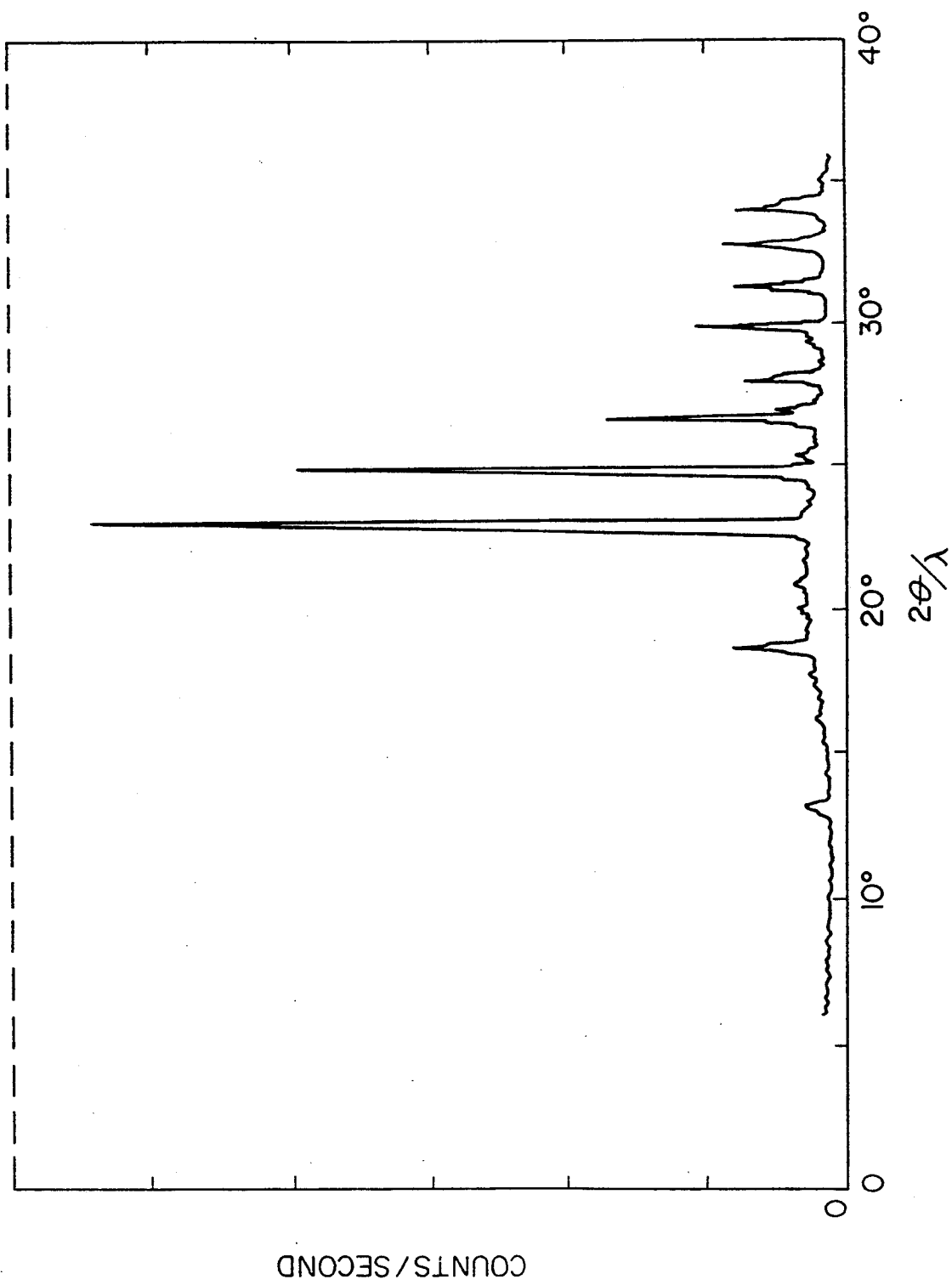

The set of "d" spacings in a particular material, along with the associated intensities of diffraction, provide a fingerprint of the material. The system simply recognizes a stored pattern as an indication that a given material is present. FIGS. 3a, 3b and 3c show examples of spectra of three particular explosives, namely trinitrotolumine (TNT), so called "C4" plastic explosive, and "Flex-x", respectively. These spectra show peaks which distinctly identify these explosives.

Figure 4:
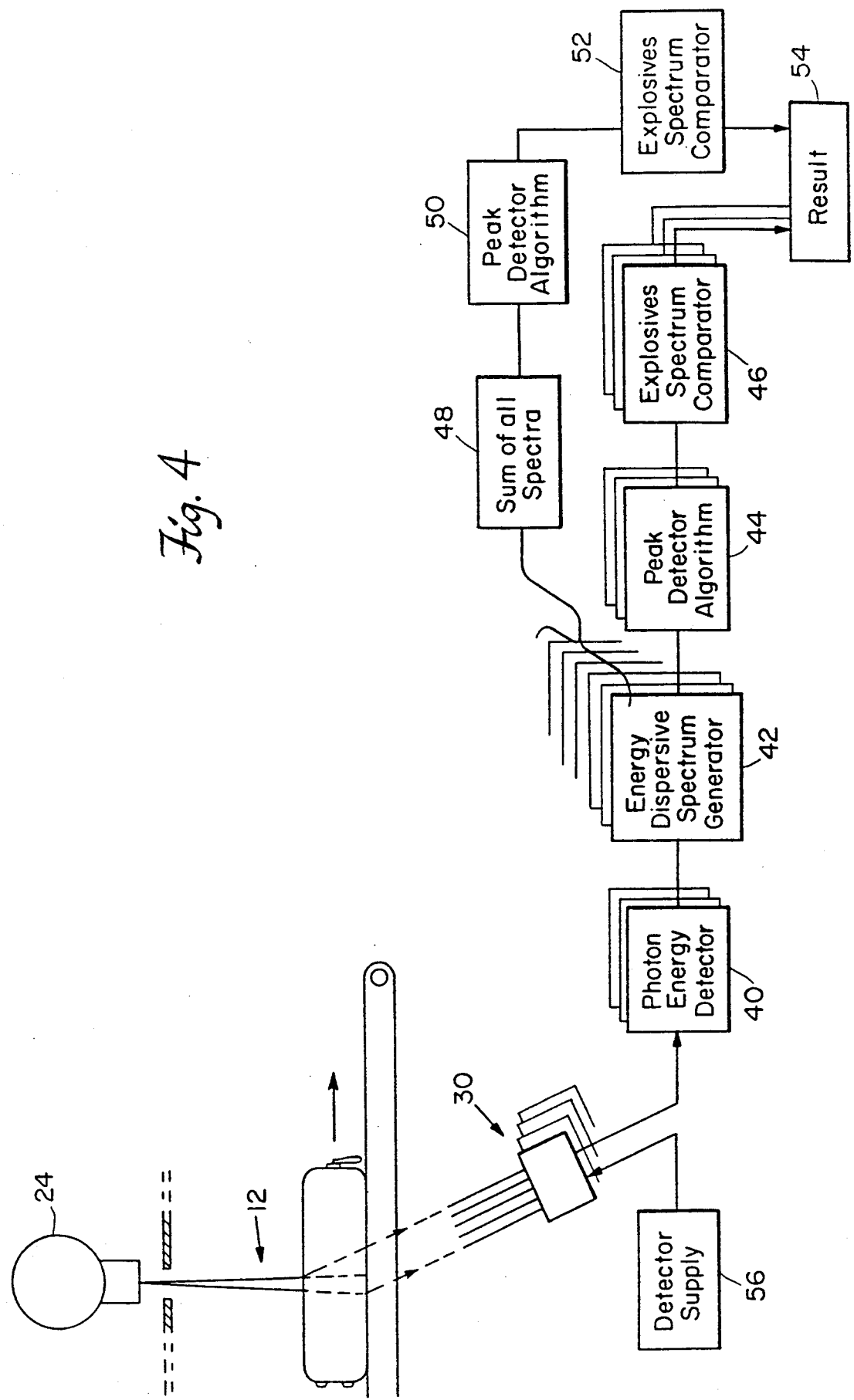
FIG. 4 is a schematic diagram of the processing system of a preferred embodiment of the invention.

FIG. 4 illustrates the processing system of a preferred embodiment in greater detail. The collimated germanium detector system 30 is used with an x-ray generator 24 capable of operating at up to 160 KV. A narrow beam 12 of x-rays is generated which irradiates a container 14 holding an explosive. The photons scattered through a fixed angle of $2\theta$ were detected and all other scatter angles were precluded by a narrow aperture collimator 34 (FIG. 2). Thus spectrum of x-rays emerges from the source 10, but only those scattered at or near an angle of $2\theta$ are seen by the detector.

A detector supply 56 provides the high voltage and temperature control system necessary to operate the germanium detector array 30. For each x-ray photon incident upon the detector, an electrical pulse is produced proportional to the energy, and therefore inversely proportional to the wavelength.

The photon energy detector 40 operates as a charge integrator which produces a digitized signal which is then processed by the spectrum generator 42. The generator 42 actually counts the number of photons within each of a number of energy intervals for each detector 32. For example, there are 140 separate 500 eV intervals in an energy range between 50 KeV and 120 KeV. Thus each detector 32 generates a spectrum displaying the number of photons counted for an inspected item as a function of photon energy.

The processing sequence is then split into two paths. The outputs from each individual spectrum generator 42 are processed by a peak detector algorithms 44 along one of these paths. Each algorithm 44 identifies those peaks within the spectrum from spectrum generator 42 which can be distinguished from the background spectra. The identified peaks are then isolated and quantified and output as a peak spectrum. The spectrum generated by the algorithm 44 for the individual detectors is then compared using the spectrum comparator 46 with a number of predetermined spectra similar to those shown in FIGS. 3a, b and c. A sufficiently close match between the peak spectrum and one or more of the stored spectra will then identify the materials detected and display the result 54.

A second processing path that can be performed simultaneously with the above processing sequence takes the output from each spectrum generator 42 and sums all of the spectra at 48. The summed spectra is then analyzed with the peak detector algorithm 50 and compared to the stored spectra 52 to determine an aggregate result for the entire parcel being inspected. Thus in situations where the signal to noise ratio is too small for the individual detectors to properly identify the contents of the parcel, the summing of all the spectra will increase the ratio for materials distributed throughout the parcel sufficiently to properly identify the contents.

It is also possible to gate the detection and processing system at predetermined time intervals during the scanning of each particular bag to further increase the sensitivity of the system.

The sensitivity of the diffraction technique depends upon the total signal collected, which, in turn, is a product of the x-ray flux density F, the illuminated volume $V_i$, the time t that the sample is in the beam, and the detector aperture seen from the sample. Consider the case of a bag containing a total volume $V_e$ of explosive material, moving at a certain speed through the x-ray fan beam of width z. For simplicity assume the explosive is a rectangular block of dimensions (a)(b)(c), moving along the "a" direction.

Then, while it is in the beam the illuminated volume is:

$$V_i = (b)(c)(z),$$

and the time that it is in the beam is a/s. Consequently, $$V_i t = V_e z/s.$$

and the overall detection sensitivity from the summed spectra for the whole bag is proportional to $$F V_e z/s.$$

It is important to emphasize that this result is independent of the shape and orientation of the explosive material within the bag.

The total radiation dose received by the inspected bag is equal to the product of the x-ray flux density and the time that one point is within the beam. The radiation dose is proportional to (F)(z)/s. Note that the x-ray beam properties and the bag speed appear identical in both expressions for the sensitivity and dose. This implies that, for a given acceptable radiation dose, the sensitivity is independent of inspection speed. One can increase the x-ray power and bag speed proportionally without affecting either dose or sensitivity.

The collimator slit 22 adjacent to the generator to provides a variable fan beam 12 which is scattered and detected with a number of detectors fitted with a second set of collimators 34. The detector collimators 34 will be arranged to pass x-rays which are scattered through a narrow angle, $2\theta$, from samples mounted in the beam or held in a suitcase in the beam as shown. The angular aperture of the collimators 34 is on the order of 0.03°. Thus only those rays scattered through an angle of 2 ±.03° are allowed into the detectors 32.

The detector 32 of a preferred embodiment has a detection area which is capable of detecting scattered rays from a cross section of baggage for the full depth of a large suitcase and a strip of about 20 to 30 mm wide across the bag. Several such detectors 32 are arranged across the conveyor having identical scatter angle and detect scattered rays from all of the bag volume.

We claim:

1. A method of inspecting parcels to detect the presence of selected crystalline materials in the presence of other crystalline and noncrystalline materials comprising:
   generating x-ray radiation from a source;
   conveying a parcel containing crystalline and noncrystalline materials to be inspected continuously past the source to irradiate the materials with the radiation;
   detecting radiation scattered by crystalline material within the parcel at a predetermined angle; and
   analyzing a spectrum of the detected radiation to detect the presence of a selected crystalline material on or within the parcel.

2. The method of claim 1 wherein the selected crystalline material is an explosive.

3. The method of claim 1 wherein said generating step is followed by the step of collimating the generated radiation.

4. The method of claim 1 wherein said selected crystalline material is a narcotic or hallucinogenic drug.

5. The method of claim 1 wherein said analyzing step comprises forming a signal from said detected radiation and comparing the signal with a predetermined spectrum.

6. The method of claim 5 wherein said forming step comprises comparing the detected spectrum with a background spectrum and isolating peaks within the detected spectrum not present in the background spectrum.

7. The method of claim 1 wherein said detecting step comprises measuring the scattered radiation with a plurality of detectors such that each detector measures the radiation scattered by a portion of the materials within the parcel.

8. The method of claim 7 further comprising:
   generating a plurality of signals from the radiation measured by each detector;
   forming a spectrum from each of the signals;
   summing the formed spectra to generate a summed spectrum for the parcel being scanned.

9. The method of claim 8 further comprising comparing the spectra with a predetermined spectra to determine the presence of selected crystalline materials.

10. The method of claim 9 wherein the formed spectra from each signal are compared with the predetermined spectra to determine the presence of selected crystalline materials in each portion of the parcel.

11. The method of claim 1 wherein said detecting step further comprises the step of analyzing the spectrum of detected radiation.

12. The method of claim 1 wherein said analyzing step comprises forming a signal from said detected radiation and comparing the signal with a predetermined spectrum.

13. A method of inspecting parcels to detect the presence of selected crystalline materials in the presence of other crystalline and noncrystalline materials comprising:
   generating x-ray radiation from a source;
   conveying a parcel to be inspected past the source to irradiate the parcel with the radiation; detecting radiation scattered by crystalline material within the parcel at a predetermined angle; and
   analyzing a spectrum of the detected radiation to detect the presence of a crystalline explosive on or within the parcel.

14. A method of inspecting parcels to detect the presence of selected crystalline materials in the presence of other crystalline and noncrystalline materials comprising:
   generating x-ray radiation from a source;
   conveying a parcel to be inspected past the source to irradiate the parcel with the radiation;
   detecting radiation scattered by crystalline material within the parcel at a predetermined angle; and
   analyzing a spectrum of the detected radiation to detect the presence of a crystalline narcotic or hallucinogenic drug on or within the parcel.

15. The method of claim 14 wherein said analyzing step further comprises forming a signal from said detected radiation and comparing the signal with a predetermined spectrum.

* * * * *